(12) United States Patent
Crawely

(10) Patent No.: US 7,326,930 B2
(45) Date of Patent: Feb. 5, 2008

(54) TERAHERTZ RADIATION SENSOR AND IMAGING SYSTEM

(75) Inventor: David Alexander Crawely, Cambridge (GB)

(73) Assignee: David Alexander Crawley, San Francisco, CA (US)

( * ) Notice: Subject to any disclaimer, the term of this patent is extended or adjusted under 35 U.S.C. 154(b) by 0 days.

(21) Appl. No.: 11/033,822

(22) Filed: Jan. 13, 2005

(65) Prior Publication Data

US 2005/0156110 A1 Jul. 21, 2005

(30) Foreign Application Priority Data

Jan. 19, 2004 (GB) ................ 0401276.1

(51) Int. Cl.
*G01J 5/02* (2006.01)
(52) U.S. Cl. .................. 250/341.1
(58) Field of Classification Search ........ 250/341.1
See application file for complete search history.

(56) References Cited

U.S. PATENT DOCUMENTS

| 5,894,125 | A | 4/1999 | Brener et al. |
| 6,239,866 | B1 * | 5/2001 | Bromage et al. .......... 356/5.01 |
| 6,690,001 | B2 * | 2/2004 | Jiang et al. .......... 250/214 VT |
| 6,828,558 | B1 | 12/2004 | Arnone et al. |
| 2001/0038074 | A1 | 11/2001 | Zhang et al. |
| 2001/0038471 | A1 | 11/2001 | Zhang et al. |
| 2002/0153874 | A1 | 10/2002 | Jiang et al. |
| 2003/0155512 | A1 * | 8/2003 | Arnone et al. .......... 250/341.1 |
| 2003/0165003 | A1 * | 9/2003 | Ciesla et al. ............... 359/326 |

2003/0178584 A1 9/2003 Arnone et al.

FOREIGN PATENT DOCUMENTS

| EP | 0841 548 A2 | 10/1997 |
| EP | 0864857 A1 | 9/1998 |
| EP | 1271 115 A2 | 1/2003 |
| EP | 0727671 B1 | 9/2003 |
| GB | 2350 673 | 12/2000 |
| GB | 2350673 A * | 12/2000 |
| GB | 2352512 | 1/2001 |

(Continued)

OTHER PUBLICATIONS

B.B. Hu & M.C. Nuss Imaging with Terahertz Waves, Optics Letters/ vol. 20, No. 16/ Aug. 15, 1995, Optical Soc. of America, USA.

(Continued)

*Primary Examiner*—David Porta
*Assistant Examiner*—Jessica L Eley

(57) ABSTRACT

This invention relates to apparatus and methods for sensing terahertz radiation, in particular over an area, and to terahertz radiation imaging systems.

Figure 1A:
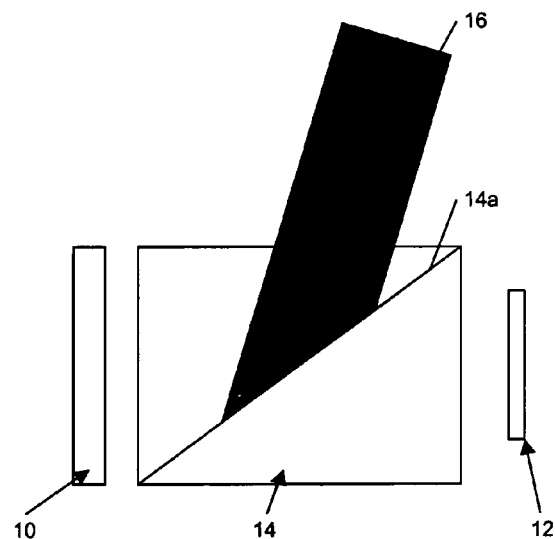

A terahertz radiation sensor, the sensor comprising an optical beam input to receive an optical probe beam, a detector to modulate said probe beam responsive to terahertz radiation, and a photosensitive detector to provide an output responsive to said probe beam modulation. The sensor being configured to provide a first optical path between said optical beam input and said electro-optic detector and to provide a second optical path between said electro-optic detector and said photosensitive detector, and wherein said sensor further comprises a polarizer, said polarizer being located in both said first and said second optical paths. We further describe imaging systems for use with such a probe.

58 Claims, 10 Drawing Sheets

FOREIGN PATENT DOCUMENTS

| | | |
|---|---|---|
| GB | 2410081 | 2/2007 |
| GB | 2425833 | 2/2007 |
| WO | WO 01/77646 A1 | 10/2001 |
| WO | WO03042070 | 5/2003 |
| WO | WO 03/095991 A1 | 11/2003 |

OTHER PUBLICATIONS

Z.G. Lu, P. Cambell & X.C. Zhang Free-space electro-optic sampling with a high-repetition-rate regenerative amplified laser, App. Phys. Lett. 71(5), Aug. 4, 1997 AIP, USA.

\* cited by examiner

TERAHERTZ RADIATION SENSOR AND IMAGING SYSTEM

CROSS-REFERENCE TO RELATED APPLICATIONS

This application claims the benefit of Great Britain application GBP290114 filed on 19 Jan. 2004.

FEDERALLY SPONSORED RESEARCH

Not Applicable

SEQUENCE LISTING OR PROGRAM

Not Applicable

BACKGROUND OF THE INVENTION—FIELD OF THE INVENTION

This invention relates to apparatus and methods for sensing terahertz radiation, in particular over an area, and to terahertz radiation imaging systems.

BACKGROUND OF THE INVENTION

The terahertz (THz) region of the electromagnetic spectrum spans the frequency range between the mid-infrared and the millimeter/microwave portion of the spectrum. In this specification, terahertz radiation is considered to be that lying within a frequency range of from 0.01 THz to 100 THz. In this specification we will also refer to light and to optical paths; it is to be understood that this includes non-visible light such as infrared and ultra violet light.

Terahertz systems have shown much promise in recent years (see, for example M. C. Beard, G. M. Turner, and C. A. Schmuttenmaer, J. Phys. Chem. B 106, 7146(2002), X.-C. Zhang, Phys. Med. Biol. 47, 3667 (2002)), however commercialization of this technology has been hampered by a lack of rugged compact imaging systems that allow rapid acquisition of terahertz images.

It has traditionally been very difficult to detect radiation in the terahertz part of the electromagnetic spectrum. Suitable detectors are typically very bulky, they often require cooling with cryogenic fluids (as with bolometric detection), and they are rarely robust and insensitive to vibration. Furthermore there are significant problems with background noise. Most objects even down to cryogenic temperatures will emit large amounts of thermal radiation in this wavelength band. It is difficult to exclude this noise in detection schemes.

Recently new schemes to detect radiation in the terahertz wavelength region have shown promise—see, for example, Hu BB, Nuss MC Imaging with Terahertz Waves, Optics Letters, 20(16), 1716 (1995). Radiation in this wavelength region induces small changes in the visible wavelength birefringence of electro-optic crystals. If terahertz radiation is provided in to an electro-optic crystal it is possible to detect its field strength by measuring the change in birefringence of the electro-optic crystal. This is known as electro-optic sampling (or EOS). Typically this birefringence change is measured by passing an optical probe pulse through the electro-optic crystal collinearly with a terahertz pulse and measuring the change in polarization of the optical pulse with a balanced diode detection scheme. It is possible by this method to coherently detect the terahertz amplitude and phase of any given terahertz pulse. This method has been employed in both biological and non-biological terahertz imaging.

If one uses ultrashort laser pulses to both generate and detect terahertz pulses this facilitates gating the EOS detection such that the detector is sensitive for only the short space of time when the sample is illuminated by the terahertz pulse. This means that the vast majority of the background radiation is excluded.

Further where the detection is coherent (i.e. the time of arrival of the terahertz pulse can be accurately measured and the entire pulse can be plotted in time) it is possible, in a pixel imaging system, to conduct spectroscopic analysis of each pixel measured in a manner analogous to FTIR.

Generally these schemes measure a single point at a time and scan the terahertz spot over the sample to measure all parts of it. However, there has been a demonstration of a system where the terahertz pulse is spread over a large area electro-optic crystal and is probed by passing an optical probe pulse over the large area of the electro-optic crystal; Lu Z G, Campbell P, Zhang X C, Free-space electro-optic sampling with a high repetition-rate regenerative amplified laser, Appl. Phys. Lett 71(5) 4, Aug. 1997. Detection of the probe pulse occurs by passing that pulse through a polarizer and then on to a CCD chip. Where the optical pulse is detected indicates where terahertz was present on the electro optic crystal.

Terahertz radiation sensors are sometimes known as terahertz probes. One design of probe is described in GB 2,352,512A, together with a number of variants of the basic design. Use of the probe to image a tooth is also described. The contents of the specification are hereby incorporated by reference in their entirety. Broadly speaking the probe of GB'512 uses electro-optic sampling along the lines described above but the device exhibits some drawbacks. One drawback relates to the sensitivity of the probe and more particularly to the size of the electro-optic response to terahertz radiation, which is very small. This, coupled with the relative lack of efficiency of terahertz emitters can result in a need to measure a change in polarization of the order of 1 part in $10^4$ to 1 part in $10^6$. The imaging device described in GB'512 (that is the device of FIG. 8) employs a liquid crystal polarizer/retarder which has an extinction ratio of the order of 1:100 and it is therefore difficult to see how such a device could be used to obtain good quality images (the device actually employed in GB'512 to capture an image employs multiple single-pixel sensors as shown in FIG. 13 rather than an array sensor). Probes which are more stable, compact, rugged and easier and cheaper to manufacture are also desirable.

A system for 3-dimensional imaging of an object using terahertz radiation is described in WO 03/042670. This describes the conventional approach to 3D imaging, that is capturing a plurality of 2D images using a point source of terahertz radiation and a terahertz-imaging sensor, rotating the object through a small angle between each (page 5, lines 1 to 6). All the terahertz probes described in GB'512 also include a terahertz lens at the front end of the probe to, essentially, image the terahertz radiation onto a sensor. Delay control is employed in GB'512 but this is merely to align the timing of the (optically) gated terahertz detector with that of the terahertz emitter.

Other background prior art is described in EP 0841548, EP 0727671, EP 0864857, U.S. Pat. No. 5,894,125, US 2001/038074 (WO 01/77646), US 2003/178584, GB 2350673, and EP 1271115. For example GB 2350673A describes a system for terahertz imaging by measuring the time of flight of a pulse through a sample, optionally Fourier transforming temporal data into the frequency domain in order to obtain a terahertz power spectrum to determine a plurality of images at different frequencies, for example to determine the composition of a structure.

Details of the time of flight technique (which assumes no diffraction) are described in GB'512 with reference to FIG. 17, the technique involving measuring the delay of a terahertz pulse passing through an object to determine the object thickness and refractive index.

SUMMARY

We will describe a probe system which uses a polarizing beam splitter. This beam splitter is preferably constructed from a birefringent crystal such as calcite or a synthetic material, although other types of polarizing beam splitter may be used.

A large spot size probe beam is inserted in to the beam splitter. The beam then reflects off an internal surface of the beam splitter and passes to the electro-optic crystal. The electro optic crystal is oriented to the polarization of the probe pulse (further details of the alignment of EOS crystals for THz generation and detection are discussed in "Generation of Terahertz Radiation from semiconductors" Thesis— University of Cambridge UK by Alessandra Corchia hereby incorporated by reference). When the terahertz pulse arrives in the EOS crystal it induces a change in the birefringence of the crystal. As a result the polarization of the optical pulse incident on the EOS crystal changes in the locations where a terahertz field is present. The beam is then reflected from a front surface of the EOS crystal; this can occur due to a change in refractive index at the surface of the EOS crystal or due to dielectric coatings in a wavelength region that allow for reflection of the probe pulse (the technology of dielectric coatings is well known to and understood by those skilled in the art). Having reflected off the front surface of the EOS crystal the probe pulse passes back through the beam splitter so that unwanted polarizations are rejected. The remaining light is detected on a photosensitive device. This device may be a CMOS or CCD chip although it is expected that a CMOS chip would provide a higher performance, lower cost system. Any kind of photosensitive array would be suitable. The areas where the visible or near infrared pulse is detected will correspond to the areas where terahertz is received on the EOS crystal.

According to a first aspect of the present invention there is therefore provided a terahertz radiation sensor, the sensor comprising an optical beam input to receive an optical probe beam a detector to modulate said probe beam responsive to terahertz radiation, and a photosensitive detector to provide an output responsive to said probe beam modulation, the sensor being configured to provide a first optical path between said optical beam input and said electro-optic detector and to provide a second optical path between said electro-optic detector and said photosensitive detector; and wherein said sensor further comprises a polarizer, said polarizer being located in both said first and said second optical paths.

If the probe pulse is already highly polarized there is no need for a polarizer in the first optical path.

In a related aspect the invention provides a terahertz radiation sensor, the sensor comprising an optical beam input to receive an optical probe beam, a detector to modulate said probe beam responsive to terahertz radiation, and a photosensitive detector to provide an output responsive to said probe beam modulation, the sensor being configured to provide a first optical path between said optical beam input and said electro-optic detector and to provide a second optical path between said electro-optic detector and said photosensitive detector; and wherein said sensor further comprises a beam splitter located in both said first and said second optical paths.

Preferably the first and second optical paths traverse the detector, which may comprise an electro-optic crystal, and are preferably substantially counter propagating within the detector. Preferably the polarizer/beam splitter comprises a polarizing beam splitter. Using a single polarizing beam splitter to both direct light onto and filter light from a detector such as an electro-optic crystal facilitates the construction of a probe head with a high extinction ratio, for example of the order of $1:10^6$. In embodiments such a configuration also facilitates fabrication of a compact and rugged probe head, as well as potentially reducing the bill of materials for the device. In embodiments the configuration also allows objects to be placed directly in front of the terahertz detector, allowing for near field imaging (Section 10.1.2 on page 437 of Optics (third edition) by Eugene Hecht describes near field (or Fresnel) diffraction and far field (or Fraunhofer) diffraction; the regimes are the same for imaging), for example where back-reflection of the probe beam by the detector is employed. Furthermore situating a polarizing beam splitter, for example comprising two trapezoid prisms, such that it both directs a probe pulse onto an electro-optic sampling crystal and filters the output from the EOS crystal makes the sensor relatively insensitive to vibration, and in embodiments, in effect makes the sensor system self-aligning.

Preferably the sensor also includes a birefringence corrector, preferably positioned so that it lies in both the first and second optical paths. This can be used to compensate for intrinsic birefringence in the detector.

The sensor is preferably configured so that the probe beam is internally reflected off a front face of the detector. This face of the detector may be provided with an optical filter to filter out ambient light which might otherwise reach the photosensitive detector and/or a multi layer stack to enhance transmission of terahertz radiation into the detector.

Preferably the photosensitive detector comprises an imaging sensor such as a CCD (charge coupled device) or CMOS (complimentary metal oxide semiconductor) sensor. Employing a photosensitive array facilitates the detection of terahertz radiation at a plurality of pixels simultaneously (area detection). This has a number of advantages in embodiments, for example, allowing faster acquisition times, allowing for single shot measurement of terahertz pulses making an imaging system less susceptible to interpulse variations and laser instability, and avoiding the need for a mechanical scanning system, thus reducing cost and complexity. A CMOS image sensing device is particularly preferred as this enables the use of higher probe beam chop rates (as described further later) thus reducing noise and improving sensitivity, as well as reducing cost and providing a more compact probe head (relative to use of a CCD sensor). Moreover in embodiments the use of CMOS detection as compared with conventional balanced diode detection can avoid the need for expensive lock-in device.

In some embodiments of the terahertz radiation sensor the sensor (front face) lacks a terahertz focusing system such as a lens or mirror and is a non-terahertz-imaging sensor (that is, the incoming terahertz radiation is not imaged, for example onto the detector). Thus the sensor may be configured that terahertz radiation falling on the detector is substantially unfocussed. This can further reduce cost and increase ruggedness and compactness of the sensor, as well as facilitating near field imaging in potentially hostile environments such as medical/veterinary endoscopic imaging. Near field imaging also potentially provides higher image resolution than available by other techniques.

Thus in another aspect the invention provides a terahertz radiation sensor comprising a terahertz detector configured to receive terahertz radiation and to provide an optical signal, and an optical image sensor coupled to said terahertz detector to provide a data output responsive to said optical signal, and wherein said detector is not in a terahertz radiation image plane.

In this context it will be understood from the description later that it is not necessary for an optical image to be formed on the optical image sensor. Thus the optical image sensor need not lie in an optical image plane compensation for this being applied, for example, by post-processing applied to the sensor output.

The invention also provides a terahertz radiation sensor, the sensor comprising an optical beam input to receive an optical probe beam, a detector to modulate said probe beam responsive to terahertz radiation, and a photosensitive detector to provide an output responsive to said probe beam modulation, the sensor being configured to provide a first optical path between said optical beam input and said electro-optic detector and to provide a second optical path between said electro-optic detector and said photosensitive detector; and wherein said sensor further comprises one or more dielectric layers on a surface of said electro-optic detector configured to enhance transmission of said terahertz radiation into said detector, a said dielectric layer comprising a material transmissive at a terahertz wavelength and having a thickness substantially equal to an odd integral number of quarter wavelengths of said terahertz radiation in said material.

There are also dielectric stack configurations that do not involve quarter wavelength thicknesses, dependent upon the number of layers deposited and their refractive index.

In a further aspect the invention provides a terahertz radiation sensor, the sensor comprising an optical beam input to receive an optical probe beam, a detector to modulate said probe beam responsive to terahertz radiation, and a photosensitive detector to provide an output responsive to said probe beam modulation, the sensor being configured to provide a first optical path between said optical beam input and said electro-optic detector and to provide a second optical path between said electro-optic detector and said photosensitive detector, and wherein said sensor further comprises a polarizing beam splitter located in both said first and said second optical paths, wherein both said first and said second optical paths traverse said detector, and wherein between said polarizing beam splitter and said detector said first and second optical paths substantially coincide.

The invention also provides terahertz imaging systems, that is systems to image an object in 2 or 3 dimensions using terahertz radiation, without necessarily imaging detected terahertz radiation. The systems include the above sensors and, in particular, may further comprise a terahertz emitter, for example controllable by an optical pulse, and means to adjust a relative timing of emission by the terahertz emitter and detection by a sensor as described above in order to determine a 2-or 3-dimensional image of an object in reflection and/or transmission.

The invention further provides a method of sensing terahertz radiation, the method comprising providing an optical probe beam to an electro-optic detector, modulating a polarization of said optical beam at said electro-optic detector using said terahertz radiation, and sensing said terahertz radiation by detecting said polarization modulation, the method further comprising polarizing said optical beam and detecting said polarization modulation using a common polarizing beam-splitter.

In a yet further aspect the invention provides a terahertz imaging system comprising a terahertz source to provide terahertz radiation for imaging an object, a terahertz sensor to detect said terahertz radiation, a timing adjust device to adjust a relative timing of emission of terahertz radiation from said source and detection of said terahertz radiation by said detector, and an image processor to receive a plurality of sensed signals from said terahertz sensor for a plurality of different said relative timings, and to output data, representing a three-dimensional image of said object determined from said plurality of sensed signals.

Such a system images or forms a representation of an object using terahertz radiation but need not (and in preferred embodiments does not) image the terahertz radiation used for imaging.

Preferably the terahertz sensor provides a 2-dimensional image output for the image processor although in other embodiments an x-y scanning system may be employed. The imaging may be performed in transmission and/or reflection; preferably the terahertz source and sensor comprise optically-controlled devices. The source may comprise a photoconductive emitter (see, for example, EP 0828143A, WO 01/38929, and the co-pending UK patent application no. GB 0307096.8 filed on 27, Mar. 2003). The sensor may comprise an electro-optic crystal, which may conveniently be driven by, for example, a common pulsed laser system with a pair of output beams and an optical timing adjust mechanism.

Broadly speaking the inventor has recognized that using successive sampling techniques, sometimes known as equivalent time sample in the context of fast digital oscilloscopes, the terahertz radiation transmitted through and/or reflected from an imaged object may not only be sensed but also characterized to, in effect, determine a wave shape of a transmitted and/or reflected E-field component of the radiation. With this information, and knowing the E-field waveshape of the terahertz radiation illuminating the imaged object, a 3-dimensional configuration of the object may be determined, by determining what 3-dimensional configuration, when applied to the illuminating radiation, gives the observed result. To perform this calculation it is not necessary that the terahertz radiation be imaged onto the radiation sensor—in effect the lack of such imaging may be taken into account by the calculation. This can be understood by thinking of the image processing as replacing the physical imaging of the terahertz radiation although, in practice, the image processor will not generally explicitly perform such a calculation.

Preferably, therefore, the terahertz sensor comprises a non-terahertz radiation imaging sensor—the terahertz detection plane (for example, the front surface of the sensor) need not be at or close to a terahertz imaging plane. The inventor has recognized that it is nonetheless possible to image an object without a physical terahertz imaging system. For example, as alluded to above, terahertz detection may be performed by phase-sensitive electro-optic sampling. As previously described in such an arrangement the probe radiation may be provided to the back of a detector crystal such an EOS crystal in order to create a phase sensitive imaging plane that can easily be sampled at multiple pixels, for example by means of a CMOS optical imaging array.

Preferably the terahertz source comprises an extended source rather than a point source. This facilitates perfusion of an object with terahertz radiation that will reach the detection plane. For some objects, such as a lens like object, perfusion of an object with terahertz radiation may be best achieved with a source that is point like, although in general a diffuse source is normally preferred.

The imaging system can be thought of as generating an interference pattern or hologram of the object (although preferably a substantially complete E-field waveform is available rather than merely amplitude and phase information) and the image processor can be thought of as reconstructing a 3-dimensional image of the object by decoding the interference pattern or hologram. Because the THz radiation tends to diffract strongly from objects with similar length scales to the terahertz radiation wavelength this method is particularly advantageous for imaging systems which contain detail on the same length scale as the terahertz wavelength.

This can be done by Fourier transforming, inverting, and then inverse Fourier transforming captured image data (although in other embodiments other transforms and inverse transforms may be employed). The captured data comprises effectively 3-dimensional data, having two spatial dimensions (x and y) and a third, time dimension (which effectively corresponds to a spatial dimension. Thus the transforms are preferably performed in three dimensions. In order to compensate for effects of the transmitted pulse shape a set of data is captured without an object present; this may then be deconvolved (in three dimensions) from data captured when an object is present. Optionally a reconstructed 3-dimensional image may be filtered or otherwise post-processed as desired.

It will be recognized that in embodiments of the above described technique a voxel of a 3D image is dependent, in general, on a complete set of captured image data (in x, y and t) rather than, say, just on a single time slice through the object. Thus preferably data representing a region of a calculated 3D image is determined from sensed signals for more than one and preferably substantially all of the plurality of different relative timings (unlike prior art techniques such as those described in GB 2350673A where, in effect, a method analogous to sonar is employed).

In a related aspect the invention provides a method of processing data from a terahertz imaging system. The method comprising inputting a plurality of sets of two-dimensional data each representing a pattern of terahertz radiation at one of a succession of sampling times of a terahertz imaging waveshape illuminating an imaged object, and generating image data representing a substantially three-dimensional image of said imaged object from said input data, wherein said generating comprises determining data for a voxel of said three-dimensional data from a plurality of said sets of two-dimensional data.

By shifting the sampling point by a few picoseconds or a few femtoseconds each time a set of 2-dimensional data is acquired a picture of the imaging waveshape as modified by the imaged object can gradually be built up and this data can then be transformed to determine a set of 3-dimensional image voxels. Optionally a priori information relating to the refractive index or refractive index range of the imaged object may be taken into account, and/or refractive index variations may be taken into account by the procedure, including absorption, that is the imaginary part of a complex refractive index.

In another aspect the invention provides a method of determining three-dimensional image data for an object using terahertz radiation. The method comprising illuminating the object with terahertz radiation having a repeated waveform, sampling, over an area, terahertz radiation transmitted and/or reflected by the object at a succession of time offsets to build up an image of said waveform after transmission through and/or reflection from said object, and determining image data for a three-dimensional image of the object which, when applied to said illuminating waveform, results in said waveform after transmission and/or reflection.

Preferably this method further comprises determining the illuminating waveform by a similar illuminating and sampling procedure without the object present.

The invention further provides systems for implementing the above described methods. Thus, in particular, the invention provides a system for determining three-dimensional image data for an object using terahertz radiation, the system comprising means for illuminating the object with terahertz radiation having a repeated waveform. Means for sampling, over an area, terahertz radiation transmitted and/or reflected by the object at a succession of time offsets to build up an image of said waveform after transmission through and/or reflection from said object, and means for determining image data for a three-dimensional image of the object which, when applied to said illuminating waveform, results in said waveform after transmission and/or reflection.

The invention also provides processor control code to implement the above described methods, in particular on a data carrier such as a disk, CD or DVD-ROM, programmed memory such as read only memory (firmware), or on a data carrier such as an optical signal carrier. Embodiments of the above described methods may be implemented using a general purpose computer system or a digital signal processor (DSP), or an application specific integrated circuit (ASIC) or field programmable gate array (FPGA). Thus code to implement embodiments of aspects of the invention may comprise code in a conventional programming language such as C, or microcode, or code for setting up or controlling an ASIC or FPGA, or code for a hardware description language such as Verilog (trademark). As the skilled person will appreciate relevant image processing code and/or data may be distributed between a plurality of coupled components in communication with one another, for example across a network.

Thus in particular the invention also provides computer program code for a terahertz imaging system comprising a terahertz source to provide terahertz radiation for imaging an object, a terahertz sensor to detect said terahertz radiation, and a timing adjust device to adjust a relative timing of emission of terahertz radiation from said source and detection of said terahertz radiation by said detector, said terahertz sensor providing a two-dimensional data output, the code being configured to, when running: capture image data from a plurality of sets of two-dimensional images of said terahertz radiation for a plurality of said relative timings, said captured image data representing an interference pattern generated by said object, and construct a three-dimensional image of said object from said captured image data by decoding said interference pattern.

In still further aspects of the invention, the above described sampling at a succession of times and means to perform this/adjust a relative timing may be replaced by sampling at a succession of frequencies and means to perform this/adjust a terahertz radiation frequency. In such a configuration, however (for example, where relatively narrowband terahertz radiation is generated, say by photo-mixing) a sampling time or time delay may still be altered to find the maximum (or maxima) of the detector's output.

The invention also provides for a means to image objects placed substantially adjacent to a plane that is sensitive to terahertz. For electro-optic sampling to be effective it is essential that the terahertz radiation and the probe radiation be co-propagating in the electro-optic sensor for this reason conventional teaching was that systems that measure terahertz by electro-optic sampling or antenna detection required the collinear insertion of probe radiation in to the terahertz sensor. The requirement that the probe beam be inserted collinearly with the terahertz pulse prevents objects to be imaged, said objects being substantially transparent to terahertz but opaque to the probe radiation, being placed in the probe beam path, and thus adjacent to the detector, see for example Lu Z G, Campbell P, Zhang X C, Free-space electro-optic sampling with a high repetition-rate regenerative amplified laser, Appl. Phys. Lett 71(5) 4, Aug. 1997. The inventor has recognized that it is in fact possible to insert the probe radiation in to the rear of the detector with the terahertz radiation configured to arrive from the front. In this case the detector is configured such that the probe radiation reflects off the front surface of the detector and from that moment on is co-propagating with the terahertz radiation. Thus the inventor has further recognized that it is possible to place objects adjacent to the detector surface. The inventor has further recognized that the ability to place objects close to the surface of the detector allows a substantial solid angle of the radiation that is reflected, scattered, or transmitted through the object to be measured. In other word the inventor has recognized that such a sensor would be able to sense terahertz in the fresnel region. The inventor has further recognized that capturing a substantial solid angle of the radiation from the object is an important pre-requisite to being able to effectively conduct imaging or inverse problem resolution using the holographic techniques that the inventor has recognized could be applied to imaging with terahertz. The inventor has further recognized that given such a sensor it may be possible to engage in other methods to reconstruct the nature of an arbitrary object placed close to the sensor that does not make strict use of the holography based techniques described herein.

DRAWINGS

Figure 1B:
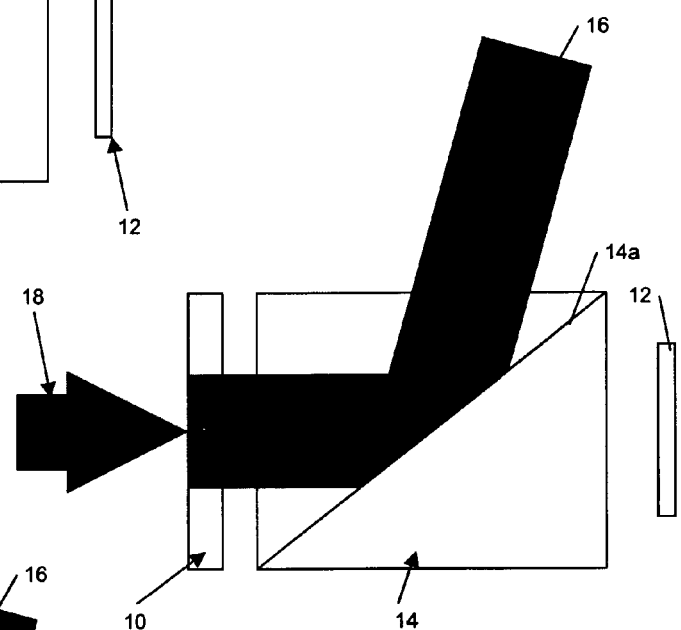
Figure 1C:
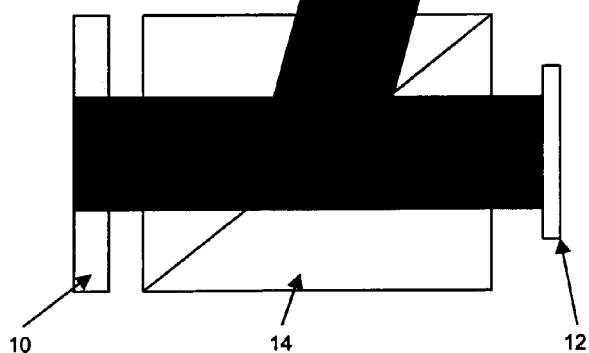
Figure 2:
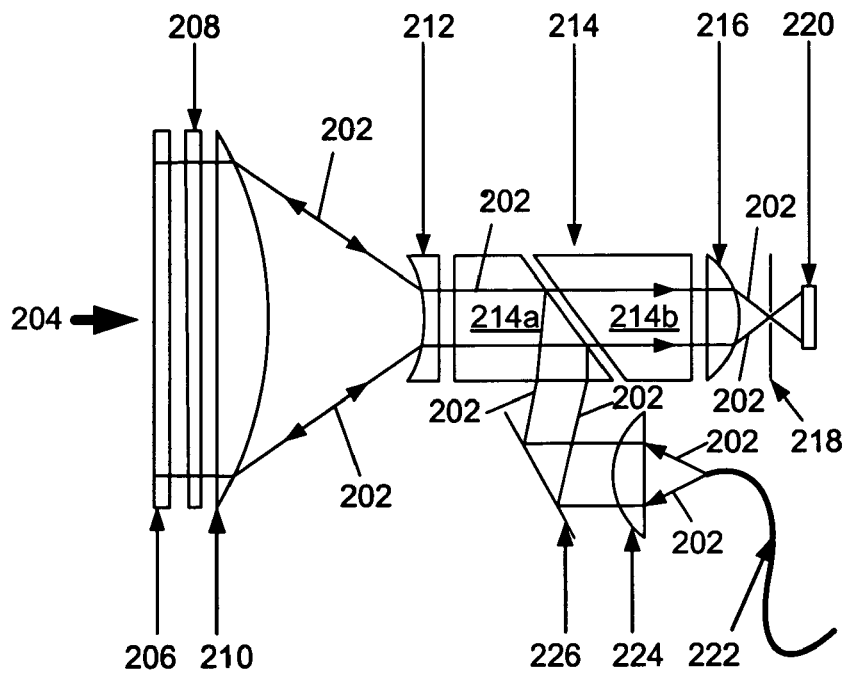
Figure 3:
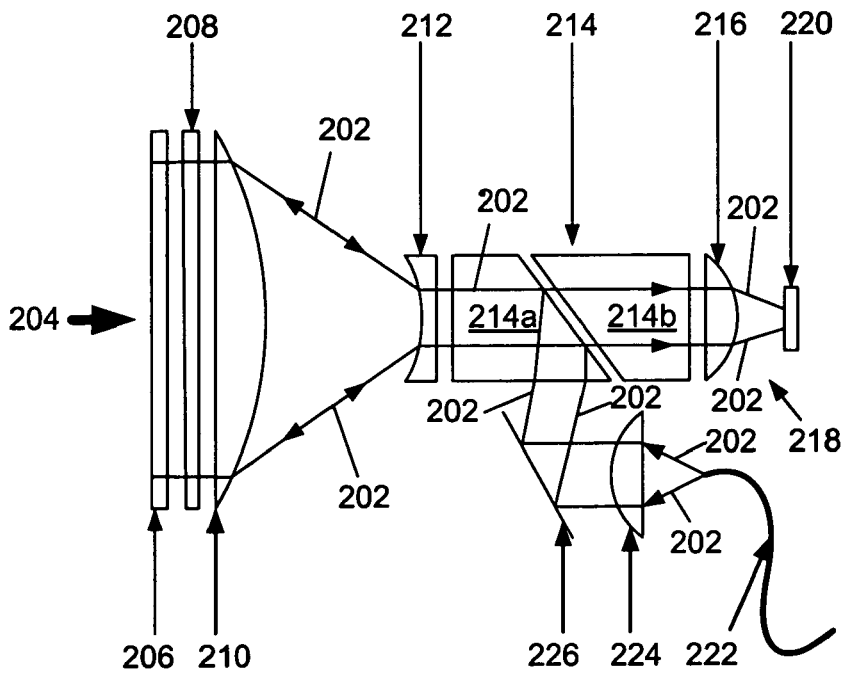
Figure 4:
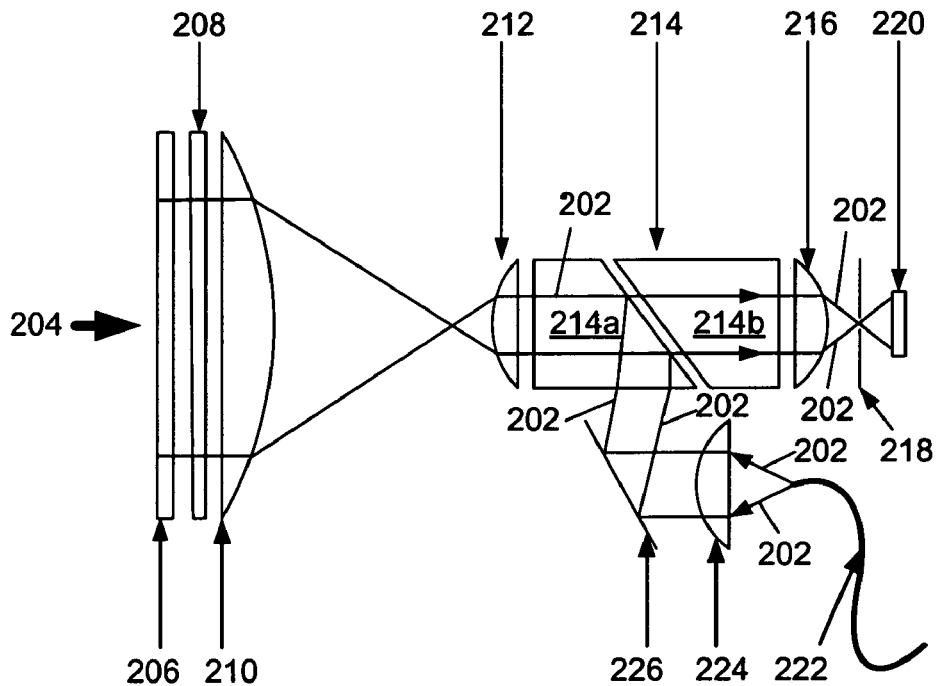
Figure 5:
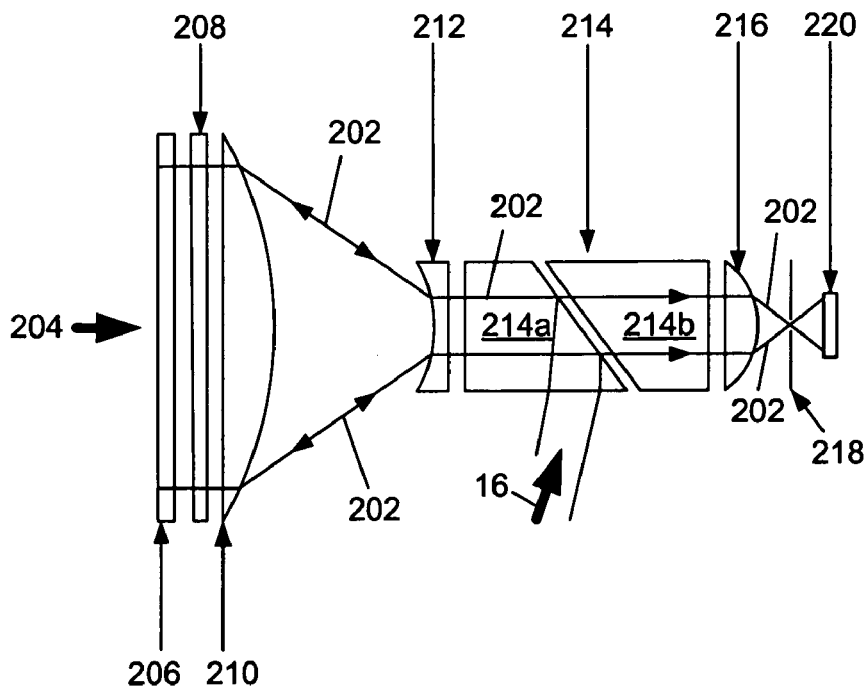
Figure 6:
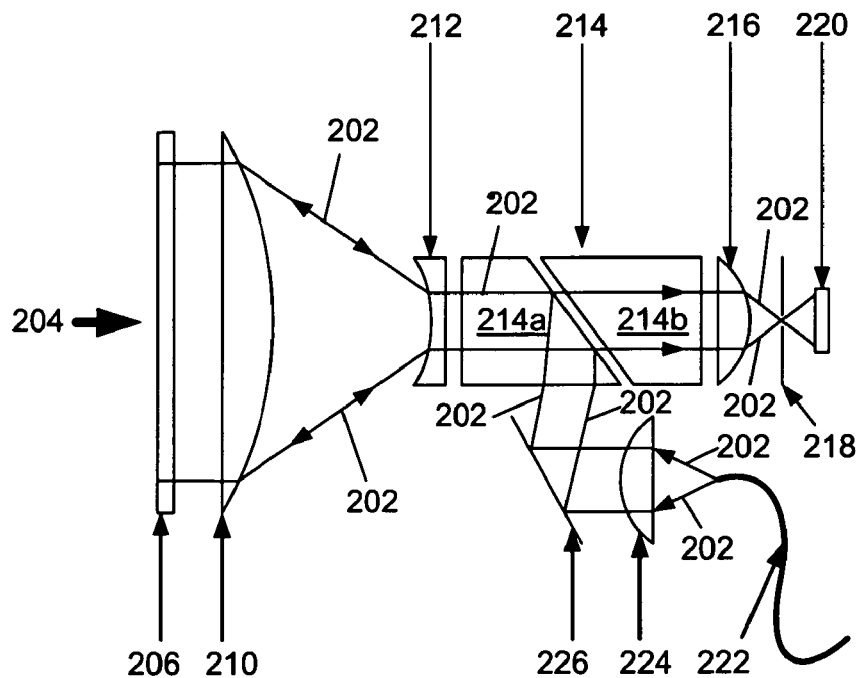
Figure 7:
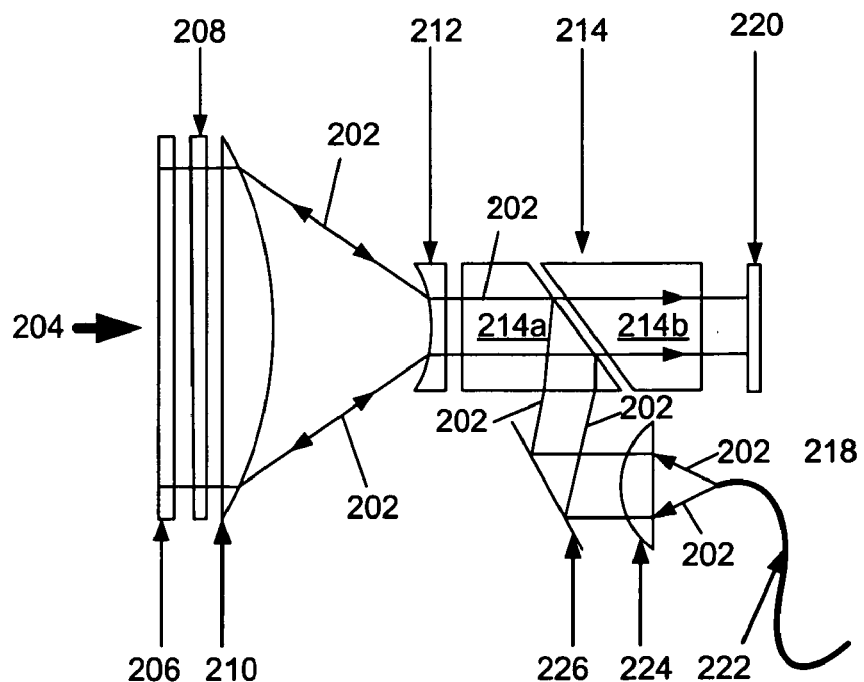
Figure 8:
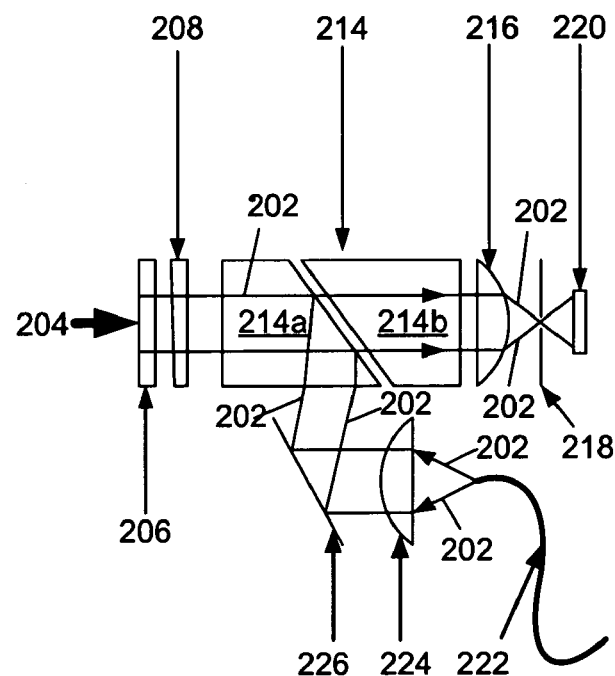
Figure 9:
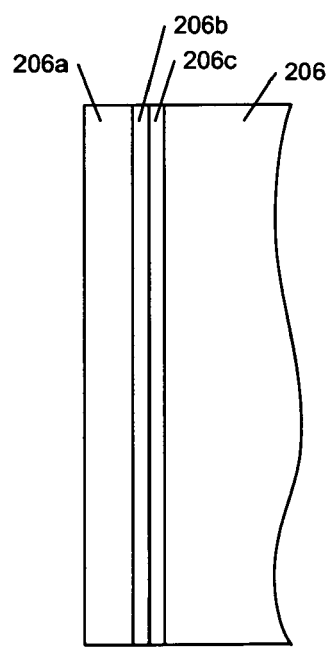
Figure 10A:
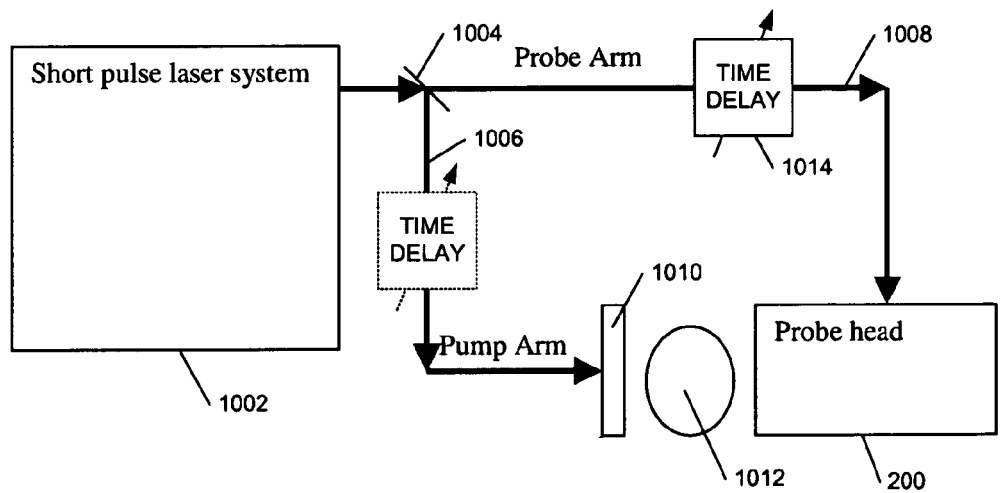
Figure 10B:
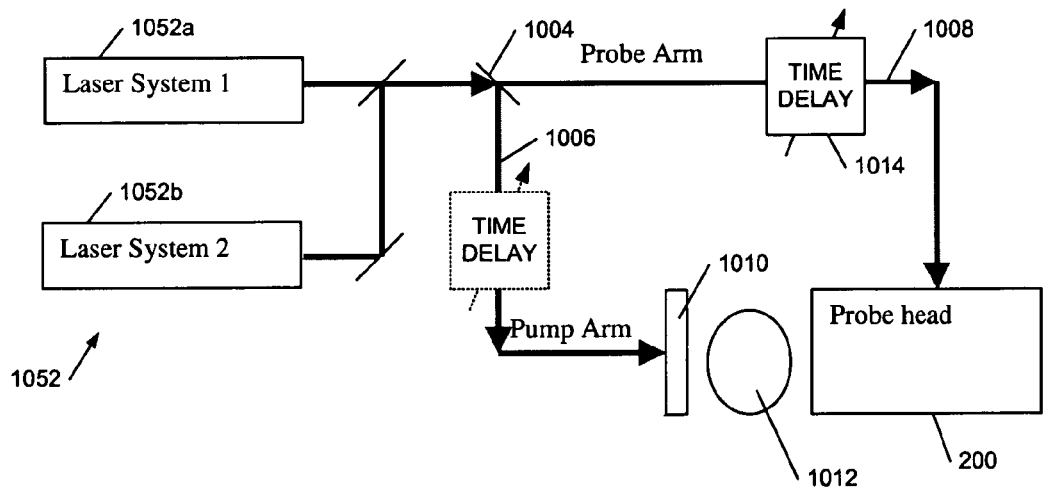
Figure 10C:
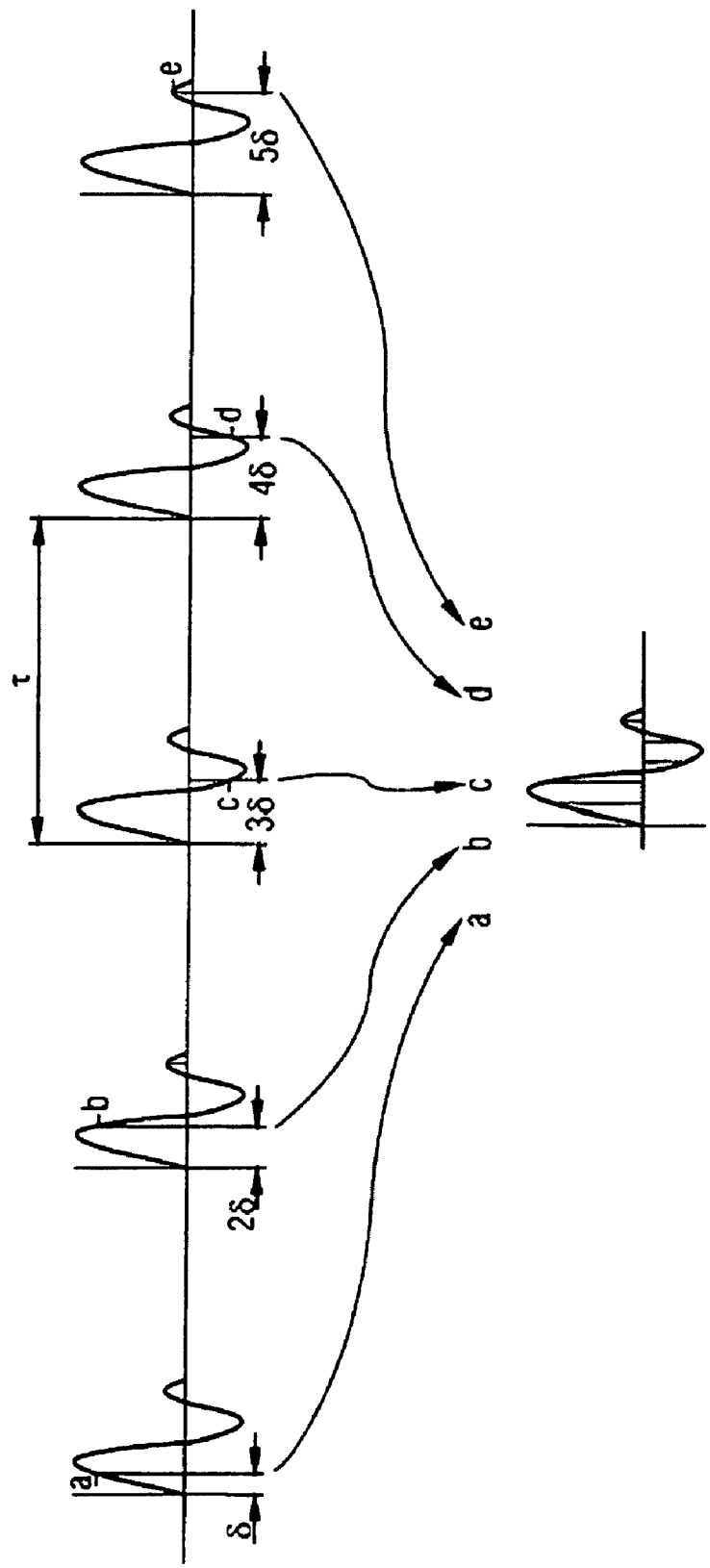
Figure 11:
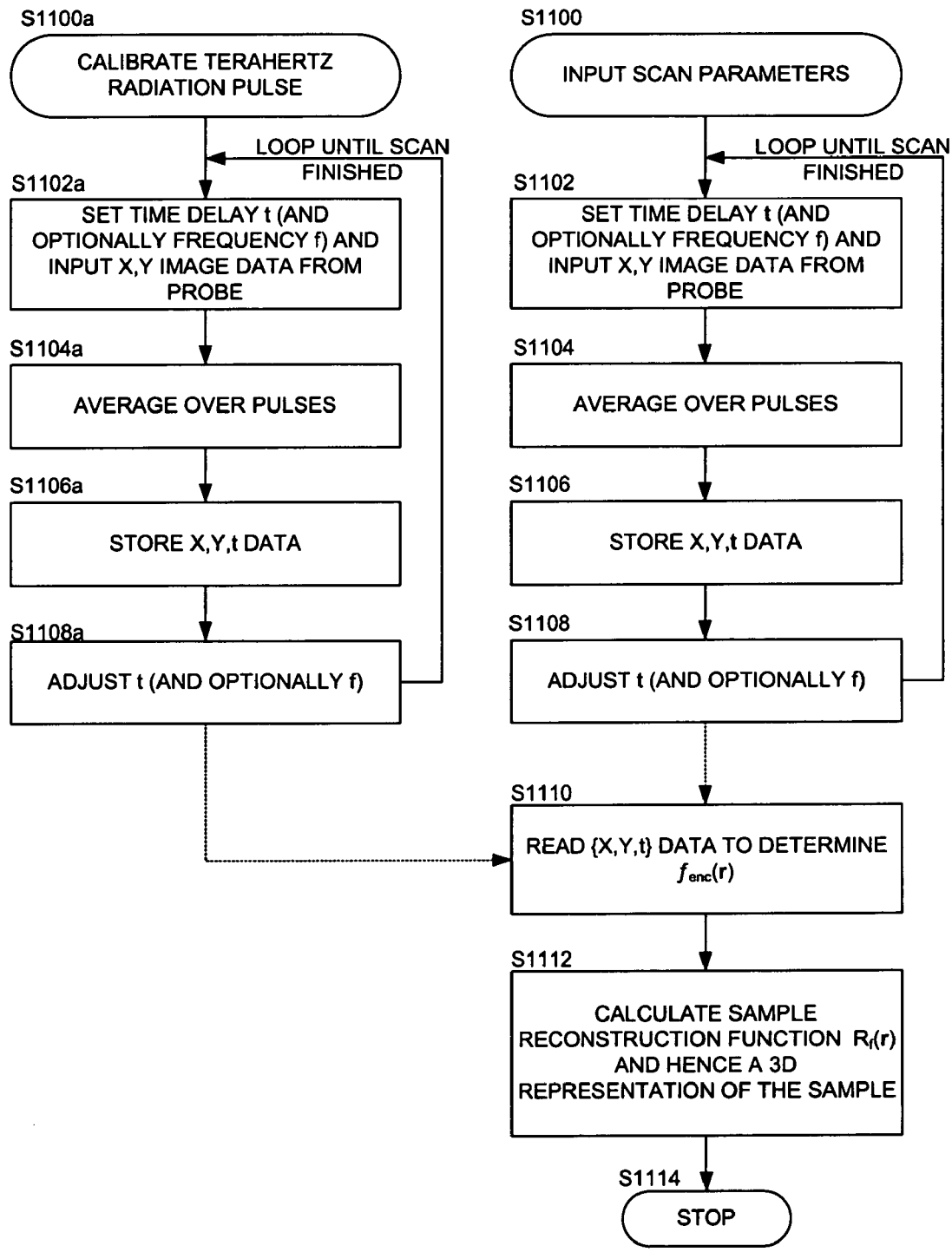
Figure 12A:
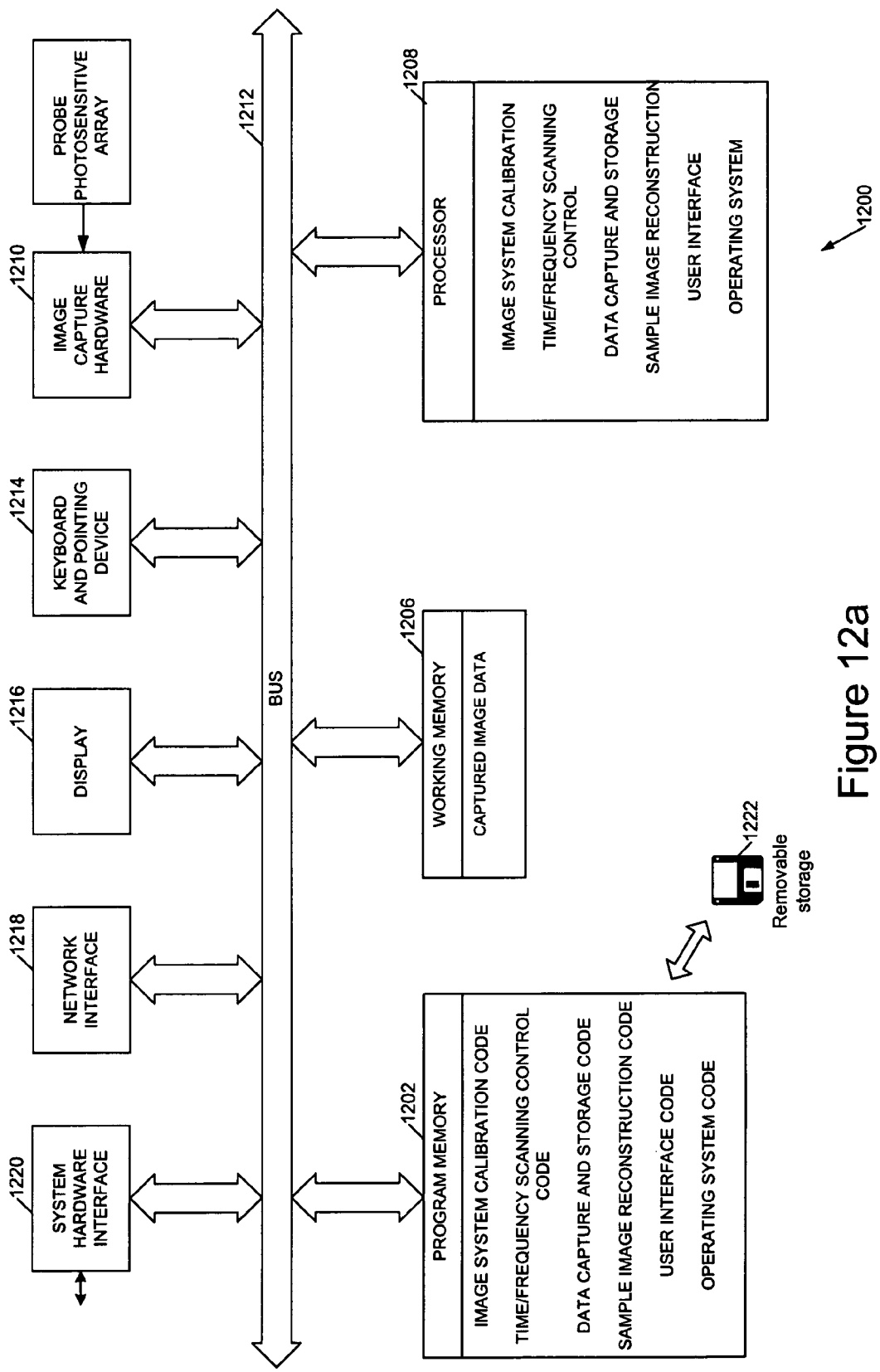
Figure 12B:
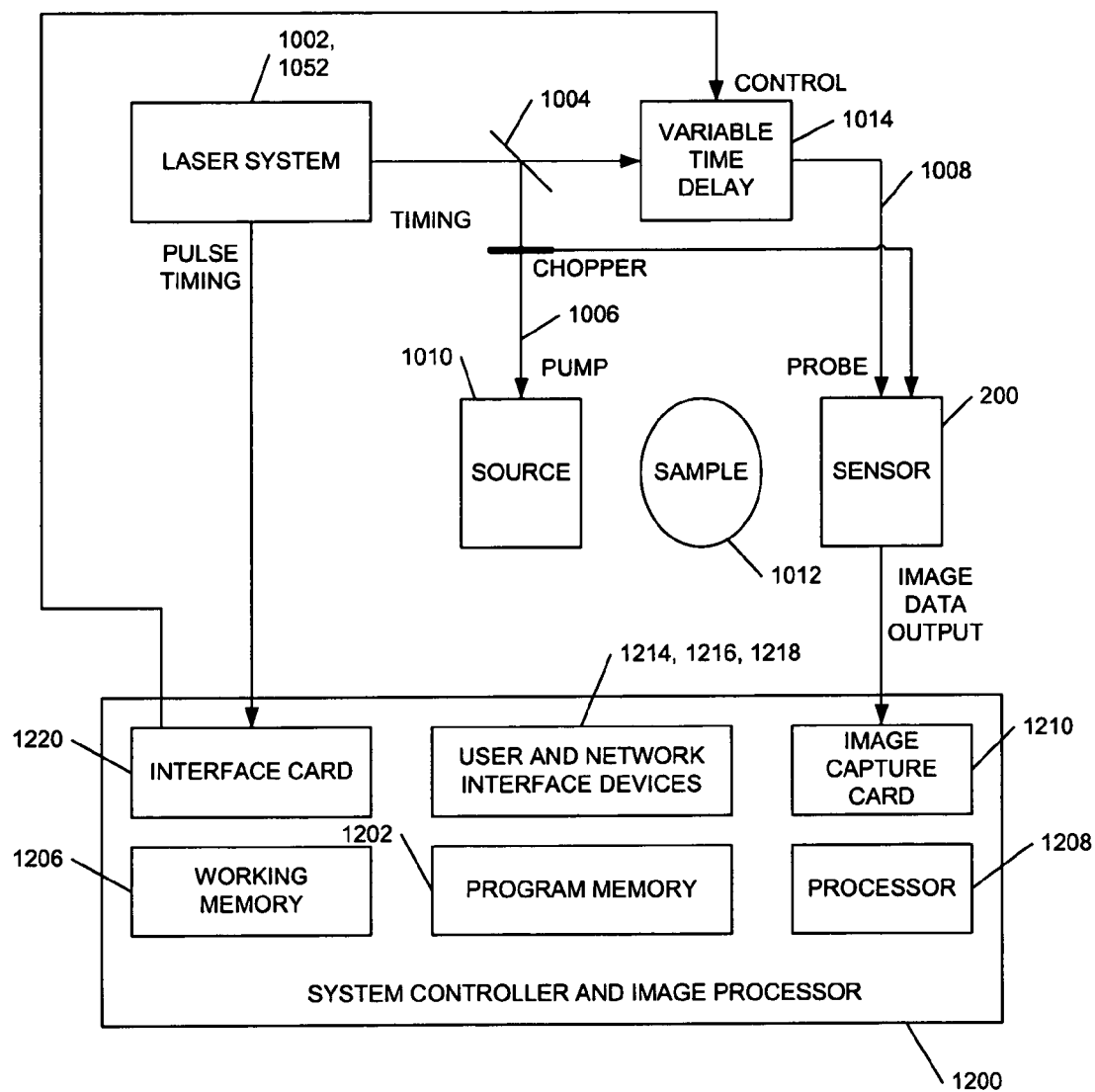

These and other aspects of the invention will now be further described, by way of example only, with reference to the accompanying figures in which:

FIGS. 1a to 1c show a simplified embodiment of terahertz radiation sensor according to an aspect of the present invention illustrating stages in the passage of a probe beam through the sensor;

FIG. 2 shows a first example of a terahertz probe head;
FIG. 3 shows a second example of a terahertz probe head;
FIG. 4 shows a third example of a terahertz probe head;
FIG. 5 shows a fourth example of a terahertz probe head;
FIG. 6 shows a fifth example of a terahertz probe head;
FIG. 7 shows a sixth example of a terahertz probe head;
FIG. 8 shows a seventh example of a terahertz probe head;
FIG. 9 shows a cross section through a front surface of a terahertz detector;
FIGS. 10a to 10c show examples of terahertz imaging systems using a short pulse laser system, and difference frequency mixing, respectively and successive sampling of terahertz pulses;
FIG. 11 shows a flow diagram for a terahertz imaging system control and processing procedure; and
FIGS. 12a and 12b show, respectively, a general purpose computer system programmed for implementing a terahertz imaging system control and image processing procedure embodying an aspect of the present invention, and a terahertz imaging system incorporating the computer system of FIG. 12a.

DETAILED DESCRIPTION

Referring to FIG. 1, a simplified terahertz radiation sensor comprises an electro-optic crystal terahertz radiation detector 10 and a photo-sensitive detector 12 between which an optical path includes a polarizing beam splitter rhomboid 14, for example a glan-laser prism (which may or may not be Brewster cut). A probe beam 16 enters the radiation sensor and is reflected by an internal interface 14a of the prism and polarized (FIG. 1a). The polarized probe beam then passes from the beam splitter 14 on to the electro-optic sampling (EOS) crystal 10, the probe beam 16 passes through the EOS crystal and is internally reflected at its front face timed to coincide with the arrival in the EOS crystal of a pulse of terahertz radiation 18 (FIG. 1b). The terahertz pulse induces a change in the birefringence of the EOS crystal such that the polarization of parts of the probe beam changes. The probe beam 16 passes through the EOS crystal and is internally reflected at its front face, then passing back through the polarizing beam splitter 14 (FIG. 1c). The parts of the beam for which the polarization has changed pass on to the photosensitive detector 12; these parts of the beam correspond to regions in the EOS crystal where terahertz radiation was detected. Other parts of the beam for which the polarization is unchanged are blocked from reaching the photosensitive detector 12. The probe pulse passes back collinearly with the THz pulse; its polarization is changed, for the most part, on the return path.

FIG. 2 shows a preferred configuration for an embodiment of a compact, rugged terahertz probe head 200 operating in accordance with the principles described above with reference to FIG. 1. Such a probe head is suitable for 2-dimensional imaging, near field and other endoscopic terahertz imaging, and quasi-holographic imaging as described further later. In an extension of this system an imaging lens or optic is provided for on the front of the sensor to enable simple 2-D imaging, for example of larger objects.

In FIG. 2 optical paths for the probe laser beam are indicated by reference 202 and incoming terahertz radiation by reference 204. The probe comprises a terahertz detector 206 such as an electro-optic crystal. In a preferred embodiment zinc telluride (ZnTe) is employed but any other suitable material may be used. (A list of suitable materials can be found in GB 2352512A, comprising materials which exhibit an AC Pockels effect, the principle upon which the detector works). Preferably the probe also includes a plate 208 in optical path 202 to correct for the intrinsic birefringence of the electro-optic crystal 206. Correction plate 208 may comprise a retarder or quarter wave plate, aligned by rotation to correct for intrinsic birefringence. Alternatively correction plate 208 may comprise another detector substantially identical to detector 206 but rotated with respect with detector 206 so as to compensate for the detector's intrinsic birefringence. In the embodiment of FIG. 2 the optical path 202 also includes a lens 210 to collimate the probe beam light onto the front surface (that is the surface facing terahertz radiation 204) of the electro-optic sampling crystal 206. A second lens 212 is provided to expand the optical beam to lens 210.

A polarizing beam splitter 214 receives incoming probe beam light and directs this towards detector 206 and also analyses the polarization of light reflected back from detector 206, providing this to a light detection system comprising, in this embodiment, a lens 216, an aperture 218, and a photosensitive array 220. Polarizing beam splitters are well known to those skilled in the art and may comprise, for example, a pair of calcite crystals 214a, b. Lens 216 focuses an optical image from detector 206 onto a photosensitive array 220 and aperture 218 is preferably included to reduce the detection of stray light. The photosensitive array 220 preferably comprises a CMOS device although CCD and other photosensitive arrays may alternatively be employed. Preferably photosensitive device 220 provides 2-dimensional image data but in other embodiments a single photosensitive diode or detector may be employed to provide a single reading of terahertz radiation detected at detector 206. In such an arrangement a 2-dimensional image may be captured by scanning the detector.

Radiation from the probe laser beam may conveniently be coupled into the terahertz probe head 200 by means of an optical fiber 222, optionally employing one or more lenses 224 to collimate and/or expand the output of the fiber. Preferably fiber 222 comprises a polarization-preserving single mode fiber although other single mode fibers may be employed as well as photonic band gap fibers (zero dispersion photonic fibers are sold by Crystal Fibre A/S—Denmark) and potentially multi-mode fibers for 2D-imaging. A mirror 226 serves to direct the collimated probe light into the polarizing beam splitter 214. Preferably mirror 226 is aligned slightly off-axis so that light that is rejected back from the probe head is not substantially coupled back into the optical fiber 222 delivering the probe radiation.

FIGS. 3 to 8 indicate alternative configurations for terahertz probe heads and in these figures like elements to those of FIG. 2 are indicated by like reference numerals. Thus FIG. 3 shows a probe head 300 with an alternative focusing arrangement for focusing probe radiation onto the photosensitive array 220. FIG. 4 shows a probe head 400 with an alternative arrangement for focusing the probe laser beam radiation onto the electro-optic sampling crystal 206. FIG. 5 shows a terahertz probe head 500 in which the probe beam 16 is provided to the polarizing beam splitter 214 through space rather than via a fiber optic. FIG. 6 shows an embodiment of a probe head 600 in which correction plate 208 is absent. FIG. 7 shows an embodiment of a probe head 700 in which lens 216 and aperture 218 are absent and in which an image from detector 208 is projected directly onto photosensitive array 220. FIG. 8 shows embodiment of a terahertz probe head in which optics (lenses 210, 212) to expand the probe radiation onto the electro-optic sampling crystal are absent. In yet other arrangements the corrector plate 208 may be located in other positions, for example between lenses 210 and 212 or between lens 212 and polarizing beam splitter 214. If the corrector plate transmits terahertz radiation then this may be positioned between the detector 206 and the terahertz radiation, and the probe beam may then be reflected off the front surface of the corrector plate. Suitable materials may be found by routine experiment and may include quartz, MgF, and calcite.

Broadly speaking the lenses in the arrangements of FIGS. 2 to 8 are employed to collimate or decollimate the probe light, but in connection with the imaging systems described later some or all of these lenses may be absent. For the imaging techniques we describe it is merely necessary that the probe light be directed from the electro-optic sampling crystal onto the photosensitive detector in a consistent manner. In other configurations, however, more complex lens and/or mirror systems than those depicted may be employed. Since the probe beam may be very bright optics with a very high f number may be employed (effectively in embodiments the photosensitive array has a large depth of field), giving considerable latitude in the design of the optical system. As will be understood from the imaging systems described later it is not a necessary requirement that the optical system pass an optical image from the detector 206 to the photosensitive array 220; The skilled person will further appreciate that where one or more lenses are employed any type of lens may be employed, including holographic fresnel lenses, as well as mirrors.

FIG. 9 shows a cross section through a front surface of the detector 206, showing coatings which may be applied to the detector. Thus the detector front surface is preferably provided with a contrast enhancing material 206a comprising a material which is opaque to light at wave lengths at which photosensitive detector 220 is sensitive, but which transmits (and is preferably substantially transparent to) terahertz radiation. Such materials include black cardboard and many black paints. Optionally the front surface of detector 206 may also be provided with one or more dielectric layers 206b to enhance transmission of terahertz radiation 204 to detector 206, and/or one or more dielectric layers 206c to enhance reflection of the probe laser pulse at the front surface of detector 206. The fabrication of suitable dielectric stacks at optical wavelengths is well known to those skilled in the art. The terahertz radiation transmission enhancing dielectric layer may comprise one or more dielectric layers of thickness substantially equal to an odd integral number of quarter wavelengths of the terahertz radiation in the dielectric material. One example of a material which may be employed is parylene (many firms offer parylene coating services); alternative coatings are provided by QMC Instruments based at the Physics Department of Cardiff University in the UK.

Referring now to FIG. 10a, this shows an example of a terahertz imaging system 1000 using the above described probe head. One or more lasers 1002 are employed to generate short pulses of light which are provided to a beam splitter 1004 to split the beam into a pump arm 1006 and a probe arm 1008. The pump arm 1006 is provided to a terahertz radiation generator 1010 whilst the probe arm 1008 is provided to a probe head 200 as described above. The two beams may be directed in free space or using optical fiber. In response to a pulse from laser system 1002 terahertz generator 1010 emits a pulse of terahertz radiation which propagates though an object 1012 or sample under examination to the probe head 200 which is gated by the optical pulse in the probe arm 1008 to respond to the pulse of terahertz radiation as it arrives.

The terahertz generator 1010 may comprise any terahertz generator that can be switched on a time scale which is similar to that of the pump arm pulse. Example terahertz generators include Austin switches, surface field emission devices, electro-optic crystals, difference frequency mixing devices, quantum cascade lasers, high frequency klystrons, and high frequency and multiplied gunn diodes and other terahertz emitters, optionally provided with a terahertz amplifier. One particularly advantageous form of emitter is described in the co-pending UK patent application no. GB 0307096.8 filed on 27, Mar. 2003; this describes an emitter including a beam expander to allow an object to be illuminated with terahertz radiation from what is effectively an extended rather than a point source. This is advantageous in the imaging techniques which are described below. Other techniques which can be employed to illuminate a sample such that it is perfused with terahertz radiation include the use of conventional beam expander arrangements with terahertz lenses or reflectors and optimized for THz wavelengths, and cassegrain, Newtonian and other systems. Techniques for the construction of wide aperture emitters are well established and known to those skilled in the art.

FIG. 10b shows an alternative example of a terahertz imaging system 1050 (in which like elements are indicated by like reference numerals) in which the short pulse laser system 1002 is replaced by a laser system 1052 comprising a pair of lasers 1052a, b emitting laser beams with a difference in frequency that lies in the terahertz range, these beams interfering when they come together. The two laser beams may be provided by two different laser systems, as shown in FIG. 10b, or they may be provided by a common laser cavity; either continuous wave or pulsed laser systems may be employed. Examples of terahertz generators using photomixing are described for example in "Generation and detection of coherent terahertz waves using two photomixers", S. Verghese, K. A. McIntosh, S. Calawa, W. F. Dinatale, E. K. Duerr, and K. A. Molvar., Applied Physics Letters Vol 73(26)pp. 3824-3826, Dec. 28, 1998."

In order to synchronize terahertz generation and terahertz detection a variable optical delay 1014 can be placed in either or both of the probe arm 1008 and pump 1006. This provides a basic imaging system.

An ultrafast pulse generally stretches when passed down an optical fiber; a small amount of such stretching does not significantly affect the detection/imaging described herein but to replace stretching a pulse can be prechirped; Coherent Inc of California USA sell systems to do this. Additionally or alternatively sapphire optical fiber may be employed or any fiber that preserves the pulse length of the pulse as it is transmitted down the fiber including photonic bandgap fibres.

We will next describe a more sophisticated technique in which such an optical delay is altered to sample successive terahertz pulses at steadily increasing offsets to build up an image or template of the shape of the electric field amplitude of a terahertz pulse received by the probe head. FIG. 10c represents five successive terahertz pulses and samples of a detected terahertz signal are taken at five (in this example) points a, b, c, d, and e and these are used to construct a representative template, overcoming the problem of sampling the same signal pulse at five successive time instance, which is very difficult due to the short duration of a pulse. In the imaging systems of FIGS. 10a and 10b the optical delay may take any convenient form, for example a corner cube reflector providing a trombone arm optical path, and may be varied either manually or automatically. Generally any conventional mechanical or non-mechanical optical delay line may be employed, optionally fiber-coupled.

Having captured a template of the received terahertz pulse a 3-dimensional image of the object 1012 (including terahertz refractive index variations) can be determined by solving an inverse problem to determine a representation of the object which, when applied to the transmitted terahertz radiation pulse, gives rise to the received signal. There are potentially many ways of solving this problem; the mathematics of one suitable technique are described in "Optical scanning holography as a technique for high-resolution three-dimensional biological microscopy"; Jim Swoger, Manuel Martínez-Corral, Jan Huisken, & Ernst H. K. Stelzer, J. Opt. Soc. Am. A. Vol. 19, No. 9, September 2002, 1910-1918, hereby incorporated by reference. An outline description of this procedure is given later. It will be appreciated that the inverse problem may be solved to determine a (2 or) 3-dimensional configuration of an object in either transmission or reflection or both.

It will be appreciated that with this technique it is important to make an accurate determination of the transmitted terahertz pulse shape and this can be done by making a similar set of measurements, varying the optical delay, without an object present in the arrangements of FIGS. 10a and 10b. The response of the system without an object or sample present can then be deconvolved from the response with an object present. It will be appreciated that with this technique there is no need to image the terahertz radiation, hence allowing for the many variations of probe head shown in FIGS. 2 to 8.

In order to enhance the signal-to-noise ratio the pump arm 1006 or terahertz generator 1010 of the system of FIGS. 10a or 10b can be chopped and acquisition of data from the photosensitive array of the probe head synchronized with a chopping signal. The pump arm may be chopped by any of a range of conventional techniques, for example using a chopper wheel or an acousto-optic modulator; alternatively the terahertz generator 1010 may be electrically chopped, or any other method which causes a well characterized variation in the terahertz emission to which the detection may be synchronized can be employed. On the detection side the signal from the chosen chopper may be connected to the probe head such that the photosensitive device on the probe head accumulates one frame (an "on" frame) while the terahertz generator 1010 produces terahertz radiation, and accumulates a separate frame when the terahertz generator is not generating terahertz radiation, or when it generates terahertz radiation with an opposite phase (an "off" frame). The off frame may then be subtracted from the on frames to produce an output frame comprising the terahertz signal.

To gather a complete set of data a number of output frames is collected at a plurality of different optical delays. Optionally (e.g. in a photomixing system) data may also be collected at a plurality of different terahertz frequencies, which facilitates compositional analysis of an object. This can be achieved, for example, using the imaging system of FIG. 10b by altering the output frequency of one of lasers 1052 with respect to the other to change the frequency of the teraherti radiation; in this way the system may be scanned over a range of terahertz frequencies. When one generates a terahertz pulse using a femto-second laser one generates a pulse which contains a range of frequencies, which is important for 3D imaging. The photomixer arrangement of FIG. 10b generates terahertz radiation using two optical beams of slightly different frequencies with a photomixing device. The terahertz frequency generated corresponds to the difference in the frequency between the two optical beams. Thus this arrangement only generates one terahertz frequency at a time, and in order to capture all of the 3-D data, one scans across all the relevant frequencies. This can be done by altering the frequency of one of the lasers relative to one of the others. The timing at each frequency may also be scanned.

The above described probe heads are able to provide a data set which measures terahertz intensity in two dimensions (x and y) and scanning through a set of different time delays provides a 3-dimensional data set including the time dimension. Fourier transforms can be used to determine a 3-dimensional image of the interior of an object from this 3-dimensional data set. Employing the terminology of Swoger et al. (ibid) a hologram generation process is describable by a correlation of a sample distribution with an encoding function:

$$H(r) = f_{sample}(r) f_{enc}(r),$$

where H(r) is the hologram, $f_{sample}$ is the characteristic of the sample that we want to image, $f_{enc}$ is an encoding function, r is a lateral position vector (x, y, t), and donates correlation of two scalars.

A reconstructed image of $f_{sample}$ can be generated by $$I_{rec}(r) = H(r) R_f(r),$$

where $R_f$ is a reconstruction function, for an ideal, one-to-one reconstruction of the sample given by $$R_f(r) - FT^{-1}[1/FT(f_{enc}(r)))],$$

where FT and $FT^{-1}$ denote Fourier and inverse Fourier transforms, respectively.

In practice the Fourier transforms may be applied numerically to a 3-dimensional data set captured using a probe head by means of a fast Fourier transform (FFT) to reconstruct a 3-dimensional (ideal) image of an object using these "holographic" techniques. The skilled person will appreciate that, in a conventional manner, such discrete FFTs should be implemented in such a way as to avoid division by zero. The skilled person will further appreciate that once an image of an object has been constructed the image may be filtered in many ways, for example to add a bandwidth limitation or to provide edge detection, for example by means of a Gabor filter.

In the above H comprises the effect of the sample convoluted with the encoding function. Thus if we take an image without a sample present this will give us a value of H for blank space, a suitable null value. When trying to reconstruct an image of the sample the acquisition of an image has two phases, one is taking a reference image (with no sample present), one is taking a sample image (with the sample present). In $$I_{rec}(r) = H(r) R_f(r),$$

H(r) is simply the reference image, (the same reference image may be used for multiple samples). Having thus acquired $I_{rec}(r)$ this may be viewed with 3 dimensional visualization software such as OpenDX.

Referring next to FIG. 11, this shows a flow diagram of a procedure which may be implemented in a computer program code to control a terahertz imaging apparatus to capture 3-dimensional data and to process this data to reconstruct an image of an object or sample. The procedure may be implemented in any conventional programming language, using one or more processors. For example parts of the procedure relating to apparatus control may be implemented using LABview (trademark) and parts of the procedure relating to image processing may be implemented using Matlab (trademark) or in dedicated code, for example on a DSP.

At Step S1100 a user inputs a set of parameters for a scan into the procedure and at Step S1102 a time delay t (and optionally a terahertz frequency f) are set and x-y image data are input from the terahertz probe, optionally averaged over a plurality of laser pulses (S1104). The captured 2-dimensional data is then stored, for example in an array (S1106) and then the time delay t (and optionally frequency f, depending on the scan parameters) are adjusted (Step S1108) and the procedure loops back to Step S1102 until the scan in time (and optionally frequency) is completed. Steps S1100a to S1108a may be employed to calibrate the imaging apparatus to determine the shape of a transmitted terahertz radiation pulse; Steps S1102a to S1108a correspond to Steps S1102 to S1108.

The image processing procedure begins at Step S1110 and is described in outline only; for further details reference may be made, for example, to the Swoger et al. paper. Thus at Step S1110 the procedure reads a complete set of {x, y, t} data which determines the encoding function $f_{enc}$. Then, at Step S1112, the procedure calculates the sample reconstruction function $R_f$ and from this a 3-dimensional reconstruction of the imaged sample or object; the procedure then ends at Step S1114.

FIG. 12 shows a general purpose computer system which may be employed to implement new procedure of FIG. 11. The computer system 1200 comprises a data and address bus 1212 to which are coupled a keyboard and pointing device 1214, a display 1216, a network interface 1218, an input/output card 1220 for interfacing to various parts of the imaging system hardware for controlling the imaging apparatus, for example using a general purpose interface bus (GPIB), and an image capture card 1210 for capturing an image from the photosensitive array 220 of the terahertz probe. Also coupled to bus 1212 are working memory 1206, for example storing captured image data, permanent program memory 1202 comprising non-volatile storage such as a hard disk, and a processor 1208. The program memory 1202 stores code comprising image system calibration code, time/frequency scanning control code, data capture and storage code, sample image reconstruction code, user interface code, and operating system code, and processor 1208 loads and implements this code to provide corresponding functions. Some or all of code in program memory 1202 may be provided on a removable storage medium illustratively shown by a disk 1222.

FIG. 12b shows a terahertz imaging system 1250 incorporating the general purpose computer system 1200 of FIG. 12a; in FIG. 12b like elements to those of FIGS. 10a and 10b are indicated by like reference numerals.

No doubt many effective alternatives will occur to the skilled person. For example although the described embodiments of the terahertz probe lack a terahertz radiation imaging system, such a system, for example a terahertz lens, may be included in the terahertz probe prior to detector 206. A coherent detection system (as described above) may also be used, for example, for spectroscopy, analogously to FTIR (Fourier Transform Infrared) spectroscopy.

It will be understood that the invention is not limited to the described embodiments and encompasses modifications apparent to those skilled in the art lying within the spirit and scope of the claims appended hereto.

I claim:

1. A terahertz radiation sensor, the sensor comprising:
an optical beam input to receive an optical probe beam;
an electro-optic detector to modulate said probe beam responsive to terahertz radiation; and
a photosensitive detector to provide an output responsive to said probe beam modulation;

the sensor being configured to provide a first optical path between said optical beam input and said electro-optic detector and to provide a second optical path between said electro-optic detector and said photosensitive detector, the terahertz radiation falling on said detector is substantially unfocussed.

2. A terahertz radiation sensor as claimed in claim 1 wherein said sensor further comprises: a polarizer, said polarizer being located in both said first and said second optical paths.

3. A terahertz radiation sensor as claimed in claim 2 wherein both said first and said second optical paths traverse said detector.

4. A terahertz radiation sensor as claimed in claim 3 wherein between said polarizer and said detector said first and second optical paths substantially coincide.

5. A terahertz radiation sensor as claimed in claim 2 wherein said polarizer comprises a polarizing beam splitter.

6. A terahertz radiation sensor as claimed in claim 1 wherein said sensor further comprises: a beam splitter located in both said first and said second optical paths.

7. A terahertz radiation sensor as claimed in claim 6 wherein both said first and said second optical paths traverse said detector.

8. A terahertz radiation sensor as claimed in claim 7 wherein between said beam splitter and said detector said first and second optical paths substantially coincide.

9. A terahertz radiation sensor as claimed in claim 6 wherein said beam splitter comprises a polarizing beam splitter.

10. A terahertz radiation sensor as claimed in any claim 1 further comprising a birefringence corrector in at least one of said first and second optical paths.

11. A terahertz radiation sensor as claimed in claim 10 wherein said birefringence corrector is in both said first and second optical paths.

12. A terahertz radiation sensor as claimed in claim 1 further comprising a reflecting surface, an optical path between said optical beam input and said photosensitive detector including said first and second optical paths and a reflection from said reflecting surface.

13. A terahertz radiation sensor as claimed in claim 12 wherein said reflecting surface comprises a surface of said detector.

14. A terahertz radiation sensor as claimed in claim 13 wherein said reflecting surface is provided with a reflection-enhancing treatment to enhance reflection of said probe beam.

15. A terahertz radiation sensor as claimed in claim 1 wherein said detector is configured to receive said terahertz radiation on a face of said detector, defining a front face of said detector, and wherein said detector front face is provided with a transmission-enhancing treatment to enhance transmission of said terahertz radiation into said detector.

16. A terahertz radiation sensor as claimed in claim 1 wherein said detector is provided with an optical attenuator to attenuate transmission of ambient light to said photosensitive detector.

17. A terahertz radiation sensor as claimed in claim 1 wherein said photosensitive detector comprises an imaging sensor.

18. A terahertz radiation sensor as claimed in claim 17 wherein said imaging sensor comprises a CMOS imaging sensor.

19. A terahertz radiation sensor as claimed in claim 1 wherein said detector comprises an electro-optic detector.

20. A terahertz radiation sensor as claimed in claim 1; and wherein said sensor further comprises: one or more dielectric layers on a surface of said electro-optic detector configured to enhance transmission of said terahertz radiation into said detector, a said dielectric layer comprising a material transmissive at a terahertz wavelength and having a thickness substantially equal to an odd integral number of quarter wavelengths of said terahertz radiation in said material.

21. A terahertz radiation sensor, as claimed in claim 1; and wherein said sensor further comprises: a polarizing beam splitter located in both said first and said second optical paths, wherein both said first and said second optical paths traverse said detector, and wherein between said polarizing beam splitter and said detector said first and second optical paths substantially coincide.

22. A terahertz imaging system including the terahertz radiation sensor of claim 1.

23. A terahertz radiation sensor comprising a terahertz detector configured to receive terahertz radiation and to provide an optical signal; and an optical image sensor coupled to said terahertz detector to provide a data output responsive to said optical signal; and wherein said detector is not in a terahertz radiation image plane.

24. A terahertz imaging system as claimed in claim 23 comprising: a terahertz emitter to emit terahertz radiation for detection by said sensor for imaging an object; means to adjust a relative timing of emission by said emitter and detection by said sensor; and means to determine a three-dimensional image of said object from said output of said sensor at a plurality of said relative timings.

25. A method of processing data from a terahertz imaging system including a terahertz radiation sensor as claimed in claim 23, the method comprising:

inputting a plurality of sets of two-dimensional data from the terahertz radiation sensor as claimed in claim 23, each representing a pattern of terahertz radiation at one of a succession of sampling times of a terahertz imaging waveshape illuminating an imaged object; and generating image data representing a substantially three-dimensional image of said imaged object from said input data, wherein said generating comprises determining data for a voxel of said three-dimensional data from a plurality of said sets of two-dimensional data.

26. A method as claimed in claim 25 wherein said terahertz imaging waveshape comprises a pulse and wherein said plurality of sets of two-dimensional data define a shape of said pulse after transmission through or reflection from said object.

27. A method as claimed in claim 26 wherein said generating comprises determining data for an object which when applied to said pulse results in said terahertz radiation pattern.

28. A method as claimed in claim 25 further comprising inputting source waveshape data representing said terahertz imaging waveshape in the absence of said object, and wherein said generating further comprises compensating for an illumination source using said source waveshape data.

29. A disk/CD/DVD-ROM carrying processor control code to, when running, implement the method of claim 25.

30. A method of determining three-dimensional image data for an object using terahertz radiation, the method comprising:
    illuminating the object with terahertz radiation having a repeated waveform;
    using a terahertz radiation sensor as claimed in claim 23 to sample, over an area, terahertz radiation transmitted and/or reflected by the object at a succession of time offsets to build up an image of said waveform after transmission through and/or reflection from said object; and
    determining image data for an image of the object which, when applied to said illuminating waveform, results in said waveform after transmission and/or reflection.

31. A method as claimed in claim 30 wherein said image is a three-dimensional image.

32. A method as claimed in claim 31 further comprising: determining said illuminating waveform by sampling said illuminating terahertz radiation without said object.

33. A disk/CD/DVD-ROM carrying processor control code to, when running, implement the method of claim 30.

34. A disk/CD/DVD-ROM carrying computer program code for a terahertz imaging system comprising:
    a terahertz source to provide terahertz radiation for imaging an object,
    a terahertz radiation sensor as claimed in claim 23 to detect said terahertz radiation, and
    a timing adjust device to adjust a relative timing of emission of terahertz radiation from said source and detection of said terahertz radiation by said detector, said terahertz sensor providing a two-dimensional data output, the code being configured to, when running:
        capture image data from a plurality of sets of two-dimensional images of said terahertz radiation for a plurality of said relative timings, said captured image data representing an interference pattern generated by said object; and
        construct a three-dimensional image of said object from said captured image data by decoding said interference pattern.

35. A system for determining three-dimensional image data for an object using terahertz radiation, the system comprising:
    means for illuminating the object with terahertz radiation having a repeated waveform;
    means using a terahertz radiation sensor as claimed in claim 23 for sampling, over an area, terahertz radiation transmitted and/or reflected by the object at a succession of time offsets to build up an image of said waveform after transmission through and/or reflection from said object; and
    means for determining image data for a three-dimensional image of the object which, when applied to said illuminating waveform, results in said waveform after transmission and/or reflection.

36. A terahertz imaging system comprising:
    a terahertz source to provide terahertz radiation for imaging an object;
    a terahertz sensor to detect said terahertz radiation;
    a timing adjust device to adjust a relative timing of emission of terahertz radiation from said source and detection of said terahertz radiation by said detector; and
    an image processor to receive a plurality of sensed signals from said terahertz sensor for a plurality of different said relative timings, and to output data representing an image of said object determined from said plurality of sensed signals, and wherein said image processor is configured to capture data from said sensor corresponding to an interference pattern generated by said object, and to construct said three-dimensional image of said object by decoding said interference pattern.

37. A terahertz imaging system as claimed in claim 36 wherein said terahertz sensor provides a two-dimensional data output for said image processor, and wherein said image is a three-dimensional image.

38. A teraheit imaging system as claimed in claim 36 wherein said terahertz sensor comprises a non-terahertz-radiation imaging sensor.

39. A terahertz imaging system as claimed in claim 36 wherein said terahertz source comprises an extended source.

40. A terahertz imaging system as claimed in claim 36 wherein said image processor is configured to determine output data representing a region of said object from said sensed signals for more than one of said different relative timings.

41. A terahertz imaging system as claimed in claim 40 wherein said image processor is configured to determine output data representing a region of said object from said sensed signals for substantially all said plurality of different relative timings.

42. A terahertz imaging system as claimed in claim 36 wherein said image processor is further configured to determine said output data by determining a Fourier transform of said plurality of sensed signals.

43. A terahertz radiation sensor, the sensor comprising:
    an optical beam input to receive an optical probe beam;
    a detector to modulate said probe beam responsive to terahertz radiation; and
    a CMOS photosensitive detector to provide an output responsive to said probe beam modulation; wherein said CMOS photosensitive detector is not in a terahertz radiation image plane.

44. A terahertz radiation sensor as claimed in claim 43 wherein said CMOS photosensitive detector comprises an imaging sensor.

45. A terahertz sensitive device, said device configured such that arbitrary objects are placeable, substantially adjacent to, or substantially in front of, the surface of the device that is sensitive to terahertz; and wherein said device is capable of measuring the E-field of the radiation being measured, or B-field of the radiation being measure, on time scales shorter than the period of oscillation of the radiation being measured.

46. A device as claimed in claim 45 wherein said device is capable of measuring the substantially instantaneous, E-field, or B-field, of a terahertz pulse at a substantially definite point in time.

47. A terahertz radiation sensor as claimed in claim 45 wherein said sensor can collect data from a plurality of points simultaneously.

48. A device as claimed in claim 45 wherein said sensor makes use of an optical probe beam in order to sense said radiation.

49. A terahertz radiation sensor, the sensor comprising:
    an optical beam input to receive an optical probe beam;
    an electro-optic detector to modulate said probe beam responsive to terahertz radiation; and
    a photosensitive detector to provide an output responsive to said probe beam modulation;

the sensor being configured simultaneously to provide a first optical path between said optical beam input and said electro-optic detector and to provide a second optical path between said electro-optic detector and said photosensitive detector, and wherein light travels on both said first and said second optical paths whether or not said terahertz radiation is present.

50. A terahertz radiation sensor as claimed in claim 49 wherein said sensor further comprises: a polarizer, said polarizer being located in both said first and said second optical paths.

51. A terahertz radiation sensor as claimed in claim 50 wherein both said first and said second optical paths traverse said detector.

52. A terahertz radiation sensor as claimed in claim 51 wherein between said polarizer and said detector said first and second optical paths substantially coincide.

53. A terahertz radiation sensor as claimed in claim 50 wherein said polarizer comprises a polarizing beam splitter.

54. A terahertz radiation sensor as claimed in claim 49 wherein said sensor further comprises: a beam splitter located in both said first and said second optical paths.

55. A terahertz radiation sensor as claimed in claim 54 wherein both said first and said second optical paths traverse said detector.

56. A terahertz radiation sensor as claimed in claim 55 wherein between said beam splitter and said detector said first and second optical paths substantially coincide.

57. A terahertz radiation sensor as claimed in claim 54 wherein said beam splitter comprises a polarizing beam splitter.

58. A terahertz radiation sensor as claimed in any claim 49 further comprising a birefringence corrector in at least one of said first and second optical paths.

* * * * *